US011958016B2

(12) United States Patent
Opperman et al.

(10) Patent No.: US 11,958,016 B2
(45) Date of Patent: Apr. 16, 2024

(54) DIALYSIS DEVICES AND SENSOR CAPS AND SYSTEMS AND METHODS INCORPORATING THE SAME

(71) Applicants: Pierce Biotechnology, Inc., Rockford, IL (US); Life Technologies Corporation, Carlsbad, CA (US)

(72) Inventors: Kay Opperman, Rockton, IL (US); Barbara Kaboord, Oregon, WI (US); Aaron McBride, Roscoe, IL (US); Greg Nagy, San Diego, CA (US); Sandro Klein, Irvine, CA (US); Joanna Geddes, Rockton, IL (US)

(73) Assignees: Pierce Biotechnology, Inc., Rockford, IL (US); Life Technologies Corporation, Carlsbad, CA (US)

( * ) Notice: Subject to any disclaimer, the term of this patent is extended or adjusted under 35 U.S.C. 154(b) by 924 days.

(21) Appl. No.: 16/456,778

(22) Filed: Jun. 28, 2019

(65) Prior Publication Data
US 2020/0000992 A1    Jan. 2, 2020

Related U.S. Application Data

(60) Provisional application No. 62/692,236, filed on Jun. 29, 2018.

(51) Int. Cl.
*A61M 1/16* (2006.01)
*B01D 61/24* (2006.01)
*B01D 63/08* (2006.01)

(52) U.S. Cl.
CPC ......... B01D 61/243 (2013.01); *A61M 1/1619* (2014.02); *A61M 1/1692* (2013.01);
(Continued)

(58) Field of Classification Search
CPC .............. A61M 1/1619; A61M 1/1692; A61M 2205/18; A61M 2205/3331;
(Continued)

(56) References Cited

U.S. PATENT DOCUMENTS 4,995,402 A * 2/1991 Smith .................. G01N 33/581
600/584
5,324,428 A    6/1994 Flaherty
(Continued)

FOREIGN PATENT DOCUMENTS

EP    1722882 B1    2/2010
EP    2106843 B1    8/2013
(Continued)

OTHER PUBLICATIONS

PCT/US2019/039873, Partial Search Report, dated Oct. 4, 2019.
(Continued)

*Primary Examiner* — Dirk R Bass
(74) *Attorney, Agent, or Firm* — BakerHostetler

(57) ABSTRACT

Dialysis devices include a frame defined by a plurality of sidewalls that are impermeable to a sample being dialyzed, a pair of dialysis membranes that are each associated with an opposing face of the plurality of sidewalls such that the plurality of sidewalls and the pair of dialysis membranes define a sample chamber, an outer shell surrounding at least a portion of the pair of dialysis membranes, and a cap selectively associated with the sample chamber. The cap can be selectively associated with the sample chamber via an attachment mechanism that is configured to provide aural and/or haptic feedback when the cap forms a tight association with the sample chamber. The cap can be a sensor cap having one or more probes for measuring at least one property of fluid inside and/or outside the sample chamber
(Continued)

and a transmitter for transmitting data captured at the probe(s) to a destination device.

2 Claims, 7 Drawing Sheets

(52) U.S. Cl.
CPC ......... *B01D 63/08* (2013.01); *A61M 2205/18* (2013.01); *A61M 2205/3331* (2013.01); *A61M 2205/3368* (2013.01); *A61M 2205/3553* (2013.01); *A61M 2205/50* (2013.01)

(58) Field of Classification Search
CPC .. A61M 2205/3368; A61M 2205/3553; A61M 2205/50; B01D 2315/06; B01D 61/243; B01D 61/28; B01D 63/08; B01L 2200/0631; B01L 2300/023; B01L 2300/043; B01L 2300/044; B01L 2300/046; B01L 2300/047; B01L 2300/0636; B01L 3/50825; G01N 1/4005; G01N 2001/4016
See application file for complete search history.

(56) References Cited

U.S. PATENT DOCUMENTS

| | | | |
|---|---|---|---|
| 5,503,741 A | 4/1996 | Clark | |
| 5,783,075 A | 7/1998 | Eddleman et al. | |
| 6,039,871 A | 3/2000 | Sykaluk | |
| 6,395,233 B1 * | 5/2002 | Diamond | G01N 1/4005 422/534 |
| 6,458,275 B1 | 10/2002 | Shukla et al. | |
| 6,531,061 B1 | 3/2003 | Cholewa | |
| 6,776,908 B1 | 8/2004 | Banker et al. | |
| 7,056,440 B2 | 6/2006 | Haney et al. | |
| 7,074,313 B2 | 7/2006 | Ben-Asouli et al. | |
| 8,007,668 B2 | 8/2011 | Haney et al. | |
| 8,012,350 B1 | 9/2011 | Alam | |
| 9,248,407 B2 | 2/2016 | Haney et al. | |
| 2003/0133846 A1 | 7/2003 | Ben-Asouli et al. | |
| 2005/0092666 A1 | 5/2005 | Wilson | |
| 2005/0145048 A1 | 7/2005 | Moir et al. | |
| 2005/0199550 A1 | 9/2005 | Haney et al. | |
| 2009/0200225 A1 * | 8/2009 | Haney | G01N 1/4005 210/321.6 |
| 2011/0163023 A1 | 7/2011 | Kreusch et al. | |
| 2012/0217203 A1 | 8/2012 | Haney et al. | |
| 2013/0068649 A1 | 3/2013 | Chen | |
| 2014/0076811 A1 | 3/2014 | Haney et al. | |
| 2016/0001285 A1 | 1/2016 | Kreusch et al. | |
| 2016/0206999 A1 | 7/2016 | Haney et al. | |
| 2018/0073991 A1 * | 3/2018 | Lura | G01N 21/6428 |
| 2021/0053055 A1 * | 2/2021 | Kreusch | B01L 3/50853 |

FOREIGN PATENT DOCUMENTS

| | | |
|---|---|---|
| EP | 3293513 A1 | 3/2018 |
| GB | 2506739 A8 | 10/2014 |
| WO | WO-1995008385 A1 | 3/1995 |
| WO | WO-2006055756 A2 | 5/2006 |
| WO | WO-2008002354 A1 | 1/2008 |
| WO | 2019/149765 A1 | 8/2019 |

OTHER PUBLICATIONS

PCT/US2019/039873, Search Report and Written Opinion, dated Nov. 25, 2019.
Xylem Analytics Germany Sales GMBH & Co. KG, "WTW: Free and connected—IDS goes wireless!", Aug. 2016, 4 pages.
Xylem Analytics Germany Sales GMBH & Co. KG, "WTW: Wireless IDS modules", Apr. 10, 2018, Retrieved from: https://www.wtw.com/en/products/product-categories/accessories/accessories-for-ids-measuring-system-digital/wireless-ids-modules.html, 2 pages.
International Preliminary Report on Patentability received for PCT Patent Application No. PCT/US19/39873, dated Jan. 7, 2022, 9 pages.
Office Action received for Chinese Patent Application No. 201980043443, dated Jan. 18, 2023, 12 pages.
Office Action received for Chinese Patent Application No. 201980043443.X, dated Jul. 6, 2022, 22 pages (13 pages of English Translation and 9 pages of Original Document).
Communication pursuant to Article 94(3) EPC issued in European Patent Application No. 19745378.0 dated Sep. 28, 2023.
Rejection Decision issued in Chinese Patent Application No. 201980043443.X dated Oct. 28, 2023, with English translation.

\* cited by examiner

DIALYSIS DEVICES AND SENSOR CAPS AND SYSTEMS AND METHODS INCORPORATING THE SAME

CROSS-REFERENCE TO RELATED APPLICATIONS

This application claims priority to and the benefit of U.S. Provisional Patent Application Ser. No. 62/692,236, filed Jun. 29, 2018 and titled "DIALYSIS DEVICES AND SENSOR CAPS AND SYSTEMS AND METHODS INCORPORATING THE SAME," which is incorporated herein by this reference in its entirety.

BACKGROUND

Technical Field

The present application relates to dialysis devices, devices for sensing one or more properties of a fluid involved in the dialysis of a sample, and systems and methods incorporating the same. More particularly, the present application relates to improved dialysis devices and sensor caps for sensing properties of a sample within a dialysis device and/or of the dialysate and to systems and methods incorporating the same.

Introduction

Dialysis membranes are semi-permeable structures that have been incorporated into many research protocols as a means for the size-based separation of molecules. For example, dialysis membranes are useful in protein treatment and purification protocols to exchange sample buffers, to concentrate a sample, to desalt a sample, or even to size-separate lower molecular weight fractions. Traditionally, dialysis membranes are formed into a tube and tied or clamped at each end to hold a sample, and the tube is then partially submerged in the desired dialysate for a period of time. Because the dialysis membranes are flexible, forming, filling, and tying a dialysis tube can require a specialized skill set and careful handling to avoid inadvertently tearing the dialysis membrane or compromising the sample. Even so, dialysis tubes are prone to leakage and can be difficult to manage.

Recent advances in dialysis systems have resulted in devices that incorporate the dialysis membranes into a sample chamber that is supported by a rigid outer body. The rigid outer body of these dialysis devices makes it easier for users to handle the enclosed samples and reduces the risk of inadvertently rupturing the dialysis membranes. However, the rigid body of current dialysis devices is bulky and requires an intricate molding and assembly process to accommodate separate pipette and syringe ports used to load and remove sample from the sample chamber. The bulk of these devices comes at the cost of additional weight. The additional weight can be offset by large air bladders incorporated into the frame, which allow the device to float when submerged in a fluid (e.g., during dialysis within a dialysate), but the large air bladders additionally contribute to the bulk and manufacturing complexity of the dialysis device.

Furthermore, the sealing caps associated with current dialysis devices are prone to accidental leakage. In some instances, leakage is the result of an over-complicated manufacturing and assembly process that causes incomplete sealing of the frame or outer cover. In other instances, leakage is the result of the sealing mechanism between the cap and the body being misaligned or malformed such that a complete seal cannot be formed there between. Even when properly manufactured and assembled, unintentional leakage can result from the misalignment of a cap during the sealing process or from overtightening and breaking the cap. Regardless of the reason for the failure, the current dialysis devices are potentially prone to accidental leakage and sensitive to raw material changes, and consequently, the sample to be dialyzed can be lost or contaminated.

The bulk, complexity, and reliability of current dialysis devices limit their utility. Accordingly, there is a need for dialysis devices that are mechanically simpler, and which provide opportunities for expanded use, among a number of additional problems and disadvantages in the field of dialysis that can be addressed.

BRIEF SUMMARY

Various embodiments disclosed herein are related to devices, methods, and systems for the dialysis of a sample. Such embodiments beneficially improve dialysis devices by, for example, simplifying the mechanical complexity of the device and its manufacturing processes to enable a lighter, less bulky device that can process the same or a greater volume of sample with a smaller footprint. As an additional example, various embodiments of dialysis devices disclosed herein beneficially provide a dialysis cap that more easily secures to the body of the dialysis device and includes aural, haptic, and/or visual feedback to indicate that a hermetic seal is formed between the cap and body—effectively reducing the occurrence of accidental leakages. As an additional example, the disclosed embodiments can increase the efficiency of systems and/or methods for dialyzing a sample by reducing sample waste and the likelihood of contamination and by providing remote monitoring of the properties of the sample and the dialysate to reduce dialysis time and to maximize workflow management.

A first aspect provides a dialysis device that includes a frame defined by a plurality of sidewalls that are impermeable to a sample being dialyzed, a pair of dialysis membranes that are each associated with an opposing face of the plurality of sidewalls such that the plurality of sidewalls and the pair of dialysis membranes define a sample chamber, an outer shell surrounding at least a portion of the pair of dialysis membranes, and a cap selectively associated with the sample chamber.

In some embodiments, a first sidewall of the frame has a concave curvature with respect to the sample chamber partially defined thereby. The concave curvature can be defined at least in part by a portion of the first sidewall that includes a peak. In some embodiments, the concave curvature is defined at least in part by an angular portion of the first sidewall that is angled toward the sample chamber at an angle less than 180°, preferably between about 90-180°, or more preferably between about 135-165°. The dialysis device can additionally include an access port in fluid communication with the sample chamber that is defined at the peak or vertex of the first sidewall. The dialysis device can additionally include a second sidewall opposite the first sidewall of the frame. The second sidewall can have a second concave curvature with respect to the sample chamber partially defined thereby and a sample collection point located at or near an inflection point or vertex of the second concave curvature. The sample collection point can be positioned such that the access port and the sample collection point are aligned.

In some embodiments, the dialysis device includes a septum associated with the access port that is made of or includes an elastic material configured to form a fluid tight seal over the access port. In some aspects, the septum includes a pierceable, self-sealing material configured to elastically deform when permitting access of a syringe or a component associated therewith to the sample chamber and to reform the fluid tight seal upon dissociation of the syringe or the component associated therewith from the septum. The cap of the dialysis device can additionally include a bottom seal having a soft material configured to form a hermetic seal over the access port when the cap associates with the sample chamber. The bottom seal can be over-molded with the cap or snappingly received within the cap.

In some embodiments, the dialysis device includes one or more float chambers that can be defined by the outer shell or included as components of the cap or as part of a body coupled to the cap. The float chambers can be at least partially filled with a buoyant material, such as a gas, an aerogel, an expanded polymeric foam, or other foam such that the buoyant material causes the dialysis device to float in a generally upright orientation when the device is immersed in a dialysate.

In some embodiments, the cap is selectively associated with the sample chamber via an attachment mechanism that is configured to provide aural and/or haptic feedback when the cap forms a tight association, such as a hermetic seal, with the sample chamber. The aural feedback can include an audible sound, such as a sharp increase in the intensity of aural feedback followed by a sharp decrease in the intensity of aural feedback upon tight association of the cap. Similarly, the haptic feedback can be any haptic feedback, such as, for example, a bump (e.g., rapid onset of haptic feedback followed by rapid decrease or cessation of haptic feedback). The device can additionally, or alternatively, include a visual cue when the cap forms a tight association with the sample chamber.

In some embodiments, the dialysis device includes a filler neck in fluid communication with the sample collection chamber. The attachment mechanism can be, for example, a set of complementary threads between the filler neck and the cap, a pin disposed on an interior surface of the cap and a horizontal channel formed by an exterior surface of the filler neck, or a pin disposed on an exterior surface of the filler neck and a channel defined by a sidewall of the cap. In some embodiments, the latter sidewall can further define a pressure ridge that is configured to (i) resist rotation of the cap about the pin, (ii) to pass into a locking portion of the aperture in response to a locking force, and (iii) to release the pin from the locking portion of the aperture in response to an unlocking force. In some embodiments, the attachment mechanism includes a hinge joint between the cap and the sample chamber. In some embodiments, the attachment mechanism includes an angled channel or aperture defined by the outer shell and a pin extending from an exterior surface of the cap, the pin configured in size and shape to fit within and engage the angled channel or aperture, to guide a rotation of the cap into association with a pressure ridge associated with the sample chamber, and to thereby cause the cap to seal the sample chamber.

In some embodiments, the cap includes a needle guide.

In some embodiments, the dialysis device includes a seal disposed between the frame and the pair of dialysis membranes. The outer shell can be ultrasonically welded together and configured to bias the pair of dialysis membranes against the seal to form a hermetic seal between the frame and the dialysis membranes. The seal can be over-molded with the frame or outer shell.

In some embodiments, the dialysis device includes a set of feet configured to enable the dialysis device to be self-standing. The set of feet can be disposed at a base of the outer shell and extend outwardly away in a direction transverse to the force of gravity when the dialysis device is in an upright orientation.

In some embodiments, the cap of the dialysis device is a sensor cap. The sensor cap can include a probe for measuring a property of a fluid within the sample chamber, such as one or more of pH, conductivity, dissolved oxygen concentration, electrical resistance, temperature, protein concentration, UV absorbance, redox potential, or turbidity. The sensor cap can additionally, or alternatively, include a second probe for measuring any of the foregoing properties, as associated with a second fluid outside the sample chamber. In embodiment, the second probe is associated with an exterior surface of the sensor cap at a position on the sensor cap to interact with and measure properties of a dialysate when the dialysis device is immersed therein. The sensor cap can additionally include one or more of a power supply, a transmitter, a receiver, a transceiver, or a communication port, such as a Bluetooth or other wireless protocol adapter. The power supply can include a rechargeable or disposable battery.

In some embodiments, the sensor cap is intended for use as a single use, disposable device. In some embodiments, a portion of the sensor cap is interchangeable or disposable.

In some embodiments, the sensor cap includes one or more processors and one or more hardware storage devices having stored thereon computer-executable instructions that when executed by the one or more processors cause the sensor cap to measure a property of the sample or of a fluid within the sample chamber and wirelessly transmit data corresponding to the measured property to a destination computing device. The computer-executable instructions can further cause the sensor cap to change a dialysis condition, such as the number of uses associated with one or more components of the sensor cap or an associated dialysis device, a stirring speed, a dialysis time, or a temperature, volume, chemistry, or concentration of one or more parts of the fluid within the sample chamber or within the dialysate. The computer-executable instructions can further cause the sensor cap to send an alert to the destination computing device based on the dialysis condition and/or to activate a second visual cue and/or aural cue to indicate the dialysis condition.

In some embodiments, the sensor cap includes an attachment mechanism configured to provide aural and haptic feedback when the sensor cap forms a tight association, such as a hermetic seal, with the sample chamber of the dialysis device. The aural feedback can include an audible sound, such as a sharp increase in the intensity of haptic feedback followed by a sharp decrease in the intensity of haptic feedback upon tight association of the sensor cap. The sensor cap can additionally include a visual cue when the sensor cap forms a tight association with the sample chamber of the dialysis device.

In some embodiments, the attachment mechanism associated with the sensor cap includes a plurality of threads disposed on an interior surface of the senor cap, a pin disposed on an interior surface of the sensor cap that is configured to interface with a horizontal channel formed by an exterior surface of a portion of the dialysis device, a hinge joint coupled to the dialysis device and integrally connected with a flexible stopper configured in size and shape to selectively seal the sample chamber of the dialysis device, or a channel defined by a sidewall of the sensor cap that is configured in size and shape to receive a pin disposed on an exterior surface of the dialysis device. In the latter embodiment, the sidewall can define a pressure ridge configured to (i) resist rotation of the sensor cap about the pin, (ii) elastically deform in response to a locking force to allow the pin to pass into a locking portion of the aperture, and (iii) elastically deform in response to an unlocking force to release the pin from the locking portion of the aperture.

Embodiments of the present disclosure additionally include systems for performing and monitoring the dialysis of a sample. In one aspect, the system includes, a dialysis device, having a frame defined by a plurality of sidewalls that are impermeable to a sample being dialyzed, a pair of dialysis membranes that are each associated with an opposing face of the plurality of sidewalls such that the plurality of sidewalls and the pair of dialysis membranes define a sample chamber, an outer shell surrounding at least a portion of the pair of dialysis membranes, and a sensor cap selectively associated with the dialysis device. The sensor cap can include one or more processors, a probe that is in electrical communication with the one or more processors and that is configured to measure a property of a fluid, a transmitter; and a power supply in electrical communication with the one or more processors, the probe, and the transmitter.

In some embodiments, the dialysis device of the system includes any of the aforementioned properties and/or components disclosed with respect to dialysis devices and/or sensor caps. Further, in some embodiments, the one or more processors of the system can additionally cause the sensor caps to perform any of the aforementioned method acts.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Figure 1:
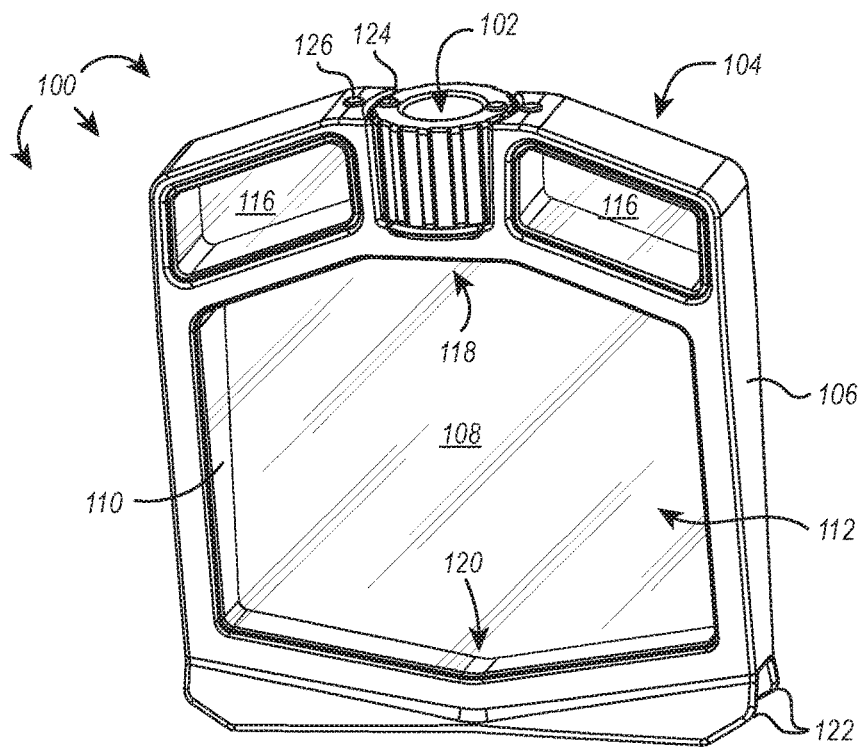
FIG. 1 illustrates a perspective view of one embodiment of a dialysis device incorporating features disclosed or envisioned herein.

As used in the specification, a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise. In addition, unless otherwise indicated, numbers expressing quantities, constituents, distances, or other measurements used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Furthermore, as used in the specification and appended claims, directional terms, such as "top," "bottom," "left," "right," "up," "down," "upper," "lower," "proximal," "adjacent," "distal," and the like are used herein solely to indicate relative directions and are not otherwise intended to limit the scope of the specification or claims.

Exemplary Dialysis Devices

Embodiments of the present disclosure include dialysis devices that solve one or more of the aforementioned problems with current dialysis devices. For example, previous dialysis devices included a pipette port positioned at the top of the sample chamber and two or more syringe ports positioned at upper corners of the sample chamber. Each syringe port required a large internal gasket to maintain a sealed sample chamber before, during, and after access by a needled syringe, and consequently, the device body needed to be adapted to accommodate the large gaskets. This resulted in a bulky body that was initially manufactured as two complementary pieces that were joined and fused together. However, due to the complex geometry of each piece, it was at times difficult or improbable to properly fuse the pieces together, which led to a weakened structural integrity and sample leakage. Prior dialysis devices also suffered from leakage due to improperly mounted caps, and although capable of standing upright on a flat surface, prior dialysis devices could easily tip over. Coupled with an improperly mounted cap, accidental tipping of prior dialysis devices additionally led to inadvertent leakage.

Figure 2:
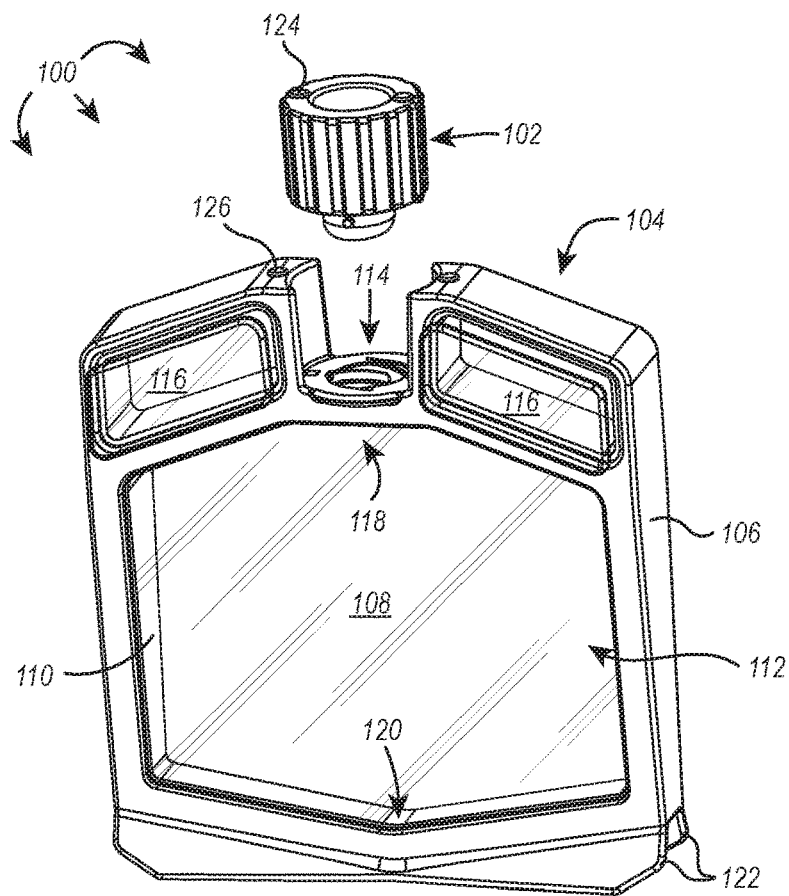
FIG. 2 illustrates a partial exploded perspective view of the dialysis device of FIG. 1.

Embodiments of the present disclosure solve one or more of the foregoing—and other—problems in the art of dialysis devices. For example, FIGS. 1 and 2 illustrate an improved dialysis device 100 of the present disclosure having improved leak-resistant properties, features that enable improved sample accessibility, and other structural elements that provide for an improved dialysis device compared to prior, known dialysis devices. FIG. 1 shows the dialysis device 100 in a fully assembled and sealed state, and FIG. 2 illustrates the same device 100 in a partially exploded state, having the cap 102 removed from the body 104. The body 104 of the dialysis device 100 of FIGS. 1 and 2 includes an outer shell 106 that secures a pair of dialysis membranes 108 to a frame 110. The frame is impermeable to sample and dialysate, and together with the dialysis membranes 108, the frame defines a sample chamber 112. The sample chamber 112 is configured to receive and retain a sample while allowing buffer, ions, and small molecules to pass through the dialysis membranes 108 and thereby dialyze the sample in accordance with a desired dialysis protocol.

As perhaps better shown in FIG. 2, the frame 110 additionally defines a dual feature access port 114 that accommodates both a syringe and pipette. In some embodiments, this dual feature access port 114—hereinafter referred to as the "access port" 114—allows for the elimination of the large internal gaskets required by the standalone syringe ports of prior dialysis devices. As a result, the dialysis device 100 is structurally and functionally simplified and provides distinct advantages over previous dialysis devices. For example, dialysis devices of the present disclosure, such as dialysis device 100 of FIGS. 1 and 2 can be manufactured using less complex structural pieces, which decreases the time and resource investment to make and assemble each dialysis device. Additionally, removal of the large gaskets allows for a slimmer, less bulky body that can be assembled with a lower occurrence and/or likelihood of leakage. For example, components of the body can be over-molded, which allows for a more compact body and additionally provides complementary surfaces of the outer shell that are more conducive to fusion, particularly ultrasonic fusion, to create a leak-resistant or leakproof body. Manufacturing and assembly processes, such as over-molding, can additionally be advantageous as they are less sensitive to raw material changes.

Further, the slimmer dialysis devices of the present disclosure, such as the dialysis device 100 of FIGS. 1 and 2, weigh less than known devices but maintain an optimal surface area to volume ratio of the sample chamber 112. When compared to known devices, the dialysis device 100 has a smaller footprint but can advantageously be used to dialyze the same volume of sample. Alternatively, if the improved dialysis devices of the present disclosure are sized similarly to the bulkier previously known dialysis devices, the improved dialysis devices can hold a greater volume of sample.

Other components of the dialysis devices disclosed herein can be adjusted to accommodate the reduced device weight to sample volume ratio described above. For example, the outer shell 106 of the dialysis device 100 shown in FIGS. 1 and 2 defines float chambers 116 that cause the dialysis device to float in a generally upright orientation when the device 100 is immersed in a dialysate. The float chambers 116 are reduced in size compared to prior devices and provide the same or similar buoyancy because of the reduction in device 100 weight. Alternatively, the float chambers could remain the same size and be used to provide greater buoyancy to the improved dialysis device or to provide the same or similar buoyancy to a greater volume of sample.

In some embodiments, the float chambers 116 are complemented by a weight (not shown) positioned on an opposite end of the float chambers 116 to encourage the dialysis device to float in a generally upright orientation. The float chambers 116 can be at least partially filled with any buoyant material such as a gas, an aerogel, an expanded polymeric foam, or other foam and can be filled to any desired level or degree to promote a desired buoyancy. As shown in FIGS. 1 and 2, an over-mold design of the body 104 defines the float chambers 116. In some embodiments, the float chambers are associated with the cap instead of the body of the dialysis device or with a float body that can be selectively or fixedly coupled to the cap.

With continued reference to FIGS. 1 and 2, the frame 110 can be defined by a plurality of sidewalls that form one or more sample collection points 118, 120 that more easily allow removal of all or nearly all of the sample from the sample chamber 112. As perhaps better illustrated in FIG. 2, a first sample collection point 118 can be defined by the sidewalls that define the access port 114 such that the first sample collection point 118 is flanked by sidewalls that slope toward the access port 114. Accordingly, if the device 100 is inverted, the sample within the sample chamber 112 will run toward the first sample collection point 118. This beneficially enables a user employing, for example, a syringe to remove sample from the sample chamber 112 more easily and more completely. As the sample—typically a liquid—is drawn out of the sample chamber 112, the curvature formed by the sidewalls flanking the first sample collection point 118 will direct the remaining sample toward the first sample collection point 118 where it can collect. In this manner, the sample will continually collect near the extraction point (e.g., the access port) and allow for a greater recovery efficiency.

The dialysis device 100 can additionally include a second sample collection point 120 that is, in some embodiments, aligned with the access port 114. Similar to the first sample collection point 118 described above, the sidewalls defining the second sample collection point 120 can be sloped toward the second sample collection point 120, and as shown in FIGS. 1 and 2, the second sample collection point 120 can be formed at the vertex of two sidewalls that form an angle directed toward the sample chamber 112 or at an inflection point of the concave curvature defined by the sidewalls. Being aligned with the access port 114, the second sample collection point 120 beneficially enables sample to be efficiently extracted from the device 100 while the device remains in an upright orientation. This can be particularly useful when extracting sample using a pipette that extends through the access port 114, as the pipette can be extended directly through the access port 114 without having to manipulate the pipette once inside the sample chamber 112. As sample is being withdrawn, the pipette can be lowered toward the second sample collection point 120 where the remaining sample will pool for extraction. In some embodiments, the first and/or second sample collection points 118, 120 can additionally be beneficial for collecting precipitates from the sample, as content precipitating from the sample can similarly be biased toward and collect at the sample collection points 118, 120 depending on the orientation of the device 100.

It should be appreciated that the length of the sidewalls and the angle formed therebetween that define the first and/or second sample collection points 118, 120 can affect the volume and surface area of the sample chamber 112. It should additionally be appreciated that the angle formed between the sidewalls that forms the first and/or second sample collection points 118, 120 can affect the efficiency of sample collection therefrom. For example, if the sidewalls forming the second sample collection point are positioned such that an acute angle is formed there between with respect to the sample chamber, a pipette used to retrieve the sample may engage the sidewalls and be mechanically restrained from reaching the vertex of the angle—and thereby be prevented from easily extracting substantially all of the sample from the sample chamber. Accordingly, in some embodiments, an angle (i.e., directed toward the sample chamber) formed by the sidewalls that define the first and/or second sample collection points is between about 90-180°. In some embodiments, the angle is between about 120-170°, preferably between about 135-165°. In some embodiments, the angle can be selected from any of the foregoing ranges based on the length of the sidewalls and the desired surface area to volume ratio of the sample chamber defined thereby.

As shown in FIGS. 1 and 2, the dialysis device 100 can additionally include a set of feet 122 that enable the dialysis device 100 to be self-standing. The set of feet 122 are disposed at a base of the outer shell 106 and extend outwardly away in a direction transverse to the force of gravity when the dialysis device 100 is in an upright orientation. This provides greater stability to the self-standing dialysis device 100 than if the feet extended in a direction parallel to the force of gravity and allows the dialysis device 100 to resist being inadvertently knocked over by glancing blows or minor perturbations to the surface on which it is standing. For example, the set of feet 122 can stabilize the dialysis device 100 in an upright orientation in response to a slight jolt from a passerby who inadvertently bumps the device 100 or the table or surface on which the dialysis device 100 stands or in response to low amplitude vibrations of equipment or other environmental sources sharing the table or surface on which the dialysis device 100 stands.

The set of feet 122 can be longer or shorter than that shown in FIGS. 1 and 2 and/or may be pitched differently to provide additional support. Additionally, or alternatively, the dialysis device can include a set of feet or multiple sets of that are each perpendicular to the force of gravity to more stably support the dialysis device in an upright orientation. For example, a dialysis device of the present disclosure can include a set of feet positioned in the middle of the device's base, aligned along a vertical axis of the dialysis device (e.g., when positioned in an upright orientation), and extending away from the dialysis device in a direction perpendicular to the force of gravity. Additional sets of feet can be placed along the base of the dialysis device and/or at opposing ends of the base. The foregoing and other disclosed sets of feet described herein can beneficially enable the dialysis device to be self-standing and can reduce the likelihood of inadvertent spillage or leakage due to the dialysis device being knocked over.

In some embodiments, the dialysis device 100 includes visual cues to reduce the likelihood of sample loss through inadvertent spillage or leakage, particularly from the cap 102 being improperly aligned or incompletely sealed to the sample chamber 112. As shown in FIGS. 1 and 2, the visual cues include raised marks 124 on the cap 102 and complementary raised marks 126 on the body 104. When the cap 102 is sealed to the body 104 (as in FIG. 1), the raised marks 124 on the cap 102 align with their complementary raised marks 126 on the body 104. This provides a quick and easy visual indication that the cap 102 is secured properly to the body 104. In the event the marks 124, 126 are misaligned (e.g., due to under tightening or misaligning the cap), the user is provided with a visual warning that the cap 102 is not properly seated or sealed to the dialysis device body 104 and can make appropriate adjustments to properly seal the cap 102 to the body 104.

In some embodiments, the visual cues are colored to enhance the visibility of the marks 124, 126. It should be appreciated, however, that the marks 124, 126 may not be raised in some embodiments but may instead be a colored indicator on the surface of the cap and body. Furthermore, although FIGS. 1 and 2 illustrate the visual cues as a pair of raised marks 124, 126 positioned on opposing sides of the cap 102 and body 104, the visual cue can be any number of raised, unraised, depressed, and/or colored marks positioned elsewhere on the cap and/or body and can be any shape. For example, the visual cue can include a single colored triangle on a side surface of the cap that aligns with a complementary colored triangle on the front the device body when the cap is secured to the body. Accordingly, visual cues incorporated into dialysis devices of the present disclosure provide an easy to recognize indicator of whether the cap is properly sealed to the dialysis device body and can thereby increase the likelihood a cap is properly secured, which in turn reduces the likelihood of sample loss through inadvertent spillage or leakage caused by an improperly sealed cap.

Additional features can be included in the dialysis device 100 to decrease spillage and/or leakage due to an improperly sealed cap 102 and/or to increase the efficiency of the device during use (e.g., by decreasing the amount of time required to properly add or remove the cap 102 from the dialysis device body 104). For example, the dialysis device 100 of FIGS. 1 and 2 can include haptic and/or aural feedback to indicate the cap 102 is properly associated with the body 104.

Figure 3:
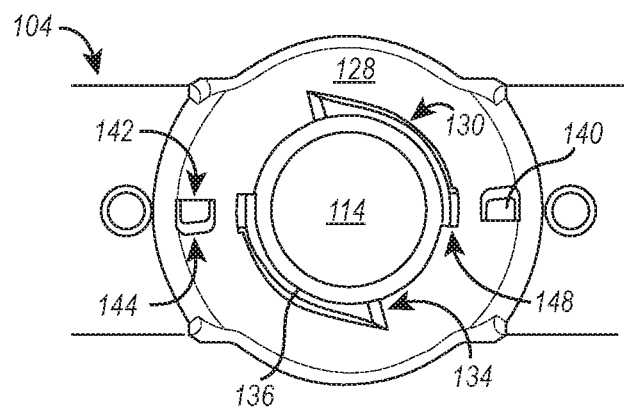
FIG. 3 illustrates a top plan view of the dialysis device of FIG. 1.
Figure 4:
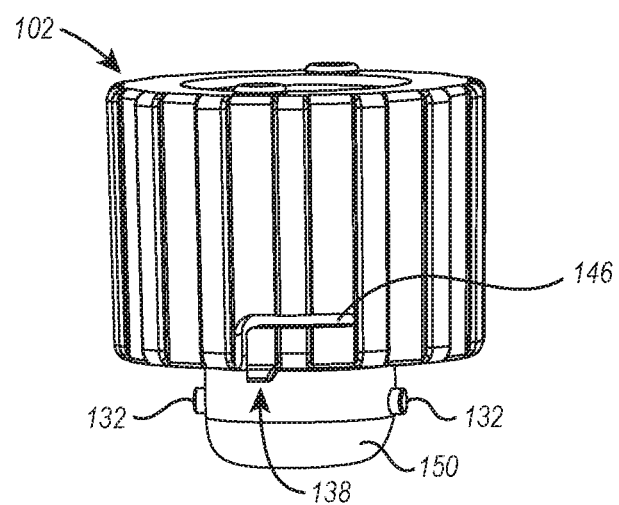
FIG. 4 illustrates a perspective view of the cap used with the dialysis device of FIG. 1.

Referring now to FIGS. 3 and 4, illustrated is a top plan view of the body 104 showing the cap seat 128 (FIG. 3), which surrounds the access port 114, and a perspective view of the cap 102 (FIG. 4), which is configured to engage the cap seat 128 and form a seal over the access port 114. As shown in FIGS. 3 and 4, the cap seat 128 includes a pair of pin guides 130 that are configured to receive pins 132 associated with the cap 102. The pin guides 130 of the dialysis device 100 are thread-like channels that start at the top surface of the cap seat 128 and wrap at least partially around the sidewall defining the access port 114, ending some distance beneath the top surface of the cap seat 128. Among other things, the pin guides 130 provide stability to the cap 102 as it is brought into tight association with the cap seat 128 and prevent the cap 102 from being pulled directly off without rotating.

In an exemplary operation, the pins 132 of the cap 102 are brought into association with the surface of the cap seat 128 where the pins 132 are corralled by the wide mouth of the guided entry point 134 and directed to a downwardly pitched ramp 136 of the pin guide 130 comprised within the channel formed into the sidewall that defines the access port 114. As the pins 132 are guided along the arcuate path of the pin guides 130, the cap 102 is brought into closer association with the cap seat 128—at which point a pair of locking elements 138 begin to engage the cap seat 128. The locking elements 138 are configured in size and shape to fit within recesses 140 formed in the surface of the cap seat 128. Further, the locking elements 138 are positioned on the cap 102 such that they engage the recesses 140 when the cap 102 is tightly secured to the cap seat 128 and forms a seal over the access port 114. Accordingly, upon tightening of the cap 102, the locking elements 138 snap into respective recesses 140 with coincident haptic and aural feedback. In some embodiments, the aural feedback presents as an audible sound, such as a click or snap. The haptic feedback can include any vibration or "bump" associated with the locking elements 138 snapping into the recesses 140, such as a sharp increase in the intensity of haptic feedback followed by a sharp decrease in the intensity of haptic feedback.

It should be appreciated that the aural and/or haptic feedback can be any type of aural/haptic feedback resulting from interactions between features of the cap 102 and the cap seat 128, specifically, or the dialysis device body 104, generally. For example, a plurality of ridges could be associated with the cap seat, and as the cap is brought into association with the cap seat, the locking element can be translocated over the plurality of ridges, resulting in haptic and aural feedback as the locking element passes each ridge. In some embodiments, the ridges increase in height as the cap tightens and consequently cause an increase in the intensity of aural and/or haptic feedback as the locking element passes over each increasingly higher ridge.

When present, the aural and/or haptic feedback provide the user with a confirmation that the cap 102 is secured properly to the cap seat 128. Accordingly, in some embodiments, the features of the cap 102 and cap seat 128 are positioned relative to each other to provide haptic and/or aural feedback when the cap 102 is tightly associated with the cap seat 128 and/or body 104 to create a seal over the access port 114. This can include, for example, matching the relative positions of the pins 132 and locking elements 138 with the positions of the guided entry point 134, the rotational distance and/or pitch of the pin guides 130, and the position of the recesses 140 so that the locking elements 138 engage respective recesses 140 following engagement of the pins 132 within the pin guide 130 and subsequent rotation of the cap to a sealed position.

For example, as shown in the exemplary embodiment of FIG. 3, the pin guides 130 each wrap at least 180° around the sidewall defining the access port 114 before the cap 102 forms a seal over the access port 114, and the recesses 140 are offset 90° from the guided entry point 134 (e.g., a first end of the pin guides 130). As such, the locking elements 138 of FIG. 3 are offset from the pins 132 by 90° so that when the pins 132 are aligned with and engage the guided entry point 134, the locking elements 138 will be positioned a 180° rotation away from respective recesses 140—the same rotational distance traversed by the pins 132 within the pin guides 130 before the cap 102 forms a seal over the access port 114.

It should be appreciated that the number of turns required to seal the access port 114 with the cap 102 can be determined by the length and pitch of the pin guides and the positions of the recesses. In some embodiments, however, the cap performs at least a quarter turn, preferably a half turn, so the pin guides can provide sufficient traction to the pins and prevent the cap from inadvertently disassociating from the cap seat.

As shown in FIG. 3, the various features of the cap seat 128 are positioned and arranged such that the cap seat 128 has rotational symmetry (e.g., an order of rotational symmetry of 2). Such rotational symmetry provides some distinct advantages, such as enabling the cap 102 to be quickly and easily associated with the cap seat 128 and doing so in a manner that encourages proper sealing of the access port 114. As provided above, the features of the cap 102 and cap seat 128 are positioned relative to each other to provide haptic and/or aural feedback when the cap 102 creates a seal over the access port 114. Having rotational symmetry, particularly an order of rotational symmetry of 2, means that the cap 102 is spun on top of the cap seat 128 at most 180° before the pins 132 are engaged and the cap sealing process begins. In some embodiments, the features of the cap and cap seat have an order of rotational symmetry of 3, which means the cap of this embodiment is spun on top of the corresponding cap seat at most 120° before the respective pins engage and the cap sealing process begins.

It should be appreciated, however, that in some embodiments, many of the foregoing advantages and functional benefits of the rotationally symmetric cap seat 128 described in FIGS. 3 and 4 can be realized without rotational symmetry of any (or every) component. For example, the cap seat could include a third recess positioned at any point between the pair of recesses 140 shown in FIG. 3 that is configured to receive a complementary third locking element on the cap. The inclusion of the third recess would destroy the rotational symmetry (i.e., reduce the rotational symmetry of the cap seat to an order of rotational symmetry of 1) of the cap seat 128 shown and described in FIG. 3, but many of the benefits associated therewith would remain. Such a cap could be quickly and easily removed and would retain the beneficial haptic and aural feedback indicative of a properly sealed cap, similar to that described for cap 102 of FIGS. 3 and 4. However, in the absence of rotational symmetry, the cap can potentially have multiple ways it can be initially associated with the cap seat but only a single orientation that will result in a properly sealed access port. The foregoing example of the cap seat having a third recess epitomizes such a situation. In this example, the cap can engage two of the three recesses with complementary locking elements in two orientations, but in only one of the two orientations will the third locking element engage the third recess and allow proper sealing of the cap.

In some embodiments, the cap can be released from the cap seat by rotating the cap in the opposite direction used to associate the cap with the cap seat. As shown in FIGS. 3 and 4, each recess 140 has a hard stop 142 configured to prevent the locking element 138 from advancing further once engaged within the recess 140 and an inclined sidewall 144 positioned opposite the hard stop 142 that is configured to permit removal of the locking element 138 from the recess 140. In an exemplary operation, a force is exerted on the cap 102 in a counter-clockwise direction to unseal and remove it from the cap seat 128. In doing so, the locking element 138 is biased against the inclined sidewall 144. A flexing gap 146 in the cap 102 allows the locking element 138 to flex and/or elastically deform upward in response to the biasing pressure exerted by the inclined sidewall 144 when the cap 102 is being unsealed. As continued or additional force is exerted on the cap 102 to unseal and remove it from the cap seat 128, the locking element 138 is disengaged from the recess 140, and the cap 102 can be freely rotated.

In some embodiments, and as depicted in FIG. 3, the cap seat 128 additionally includes a quick release channel 148 positioned along the pin guide 130 (e.g., the midpoint of the pin guide 130) and in fluid communication with the pin guide 130. The quick release channels 148 enable the cap 102, in some embodiments, to be quickly and easily removed from the cap seat 128 and in potentially fewer rotations—and consequently less time—compared to the number of rotations performed when associating the cap 102 with the cap seat 128. When implemented, the pins 132 can traverse the channel 148 vertically instead of rotating through the remainder of the pin guide 130.

In some embodiments, the quick release channel 148 can also be used to reduce the rotational distance for sealing the cap 102. However, it may take additional time and focus to accurately position the pins 132 compared to the less demanding task of allowing the guided entry points 134 to corral and guide the pins 132 into the guide channel formed by the pin guide 130. This demand is reduced or eliminated when removing the cap because the quick release channel 148 is integrally formed with the upper sidewall of the pin guide 130. If an upward force is exerted on the cap 102 during the unsealing rotations, it will force the pins 132 to ride along the upper sidewall of the pin guide 130 and seamlessly flow into the quick release channel 148 integrally formed therewith. Accordingly, the quick release channel 148 can be used to reduce the time and energy of unsealing the dialysis device 100, which can lead to greater efficiencies in the laboratory or other dialysis setting.

It should be appreciated that the force required to remove the cap can be increased or decreased as desired by adjusting, adding, or removing one or more of the cap seat components described above. For example, the force required to remove the cap can be increased by using a material for the cap that has a higher Young's modulus (and thereby stiffening the locking element), increasing the depth of the recess and the length of the locking mechanism, increasing the pitch of the inclined surface defining a portion of the recess, and/or by adding additional recess-locking mechanism pairings (while preferably maintaining rotational symmetry of the cap seat at an order of rotational symmetry of 2 or greater). Similarly, the force required to remove the cap can be reduced by using a material for the cap that has a lower Young's modulus (and thereby making the locking mechanism more elastic and easier to deform), decreasing the depth of the recess and the length of the locking mechanism, decreasing the pitch of the inclined surface defining a portion of the recess, and/or by reducing the number of recess-locking mechanism pairings on the cap seat (while preferably maintaining rotational symmetry of the cap seat at an order of rotational symmetry of at least 2).

Although the dialysis device 100 of FIGS. 1-4 was disclosed as including visual cues, haptic feedback, and aural feedback to indicate the cap 102 is properly associated with the body 104 (e.g., forming a hermetic seal over the access port 114), it should be appreciated that the dialysis devices disclosed herein can include any number, type, or combination of visual cues, haptic feedback, and aural feedback to indicate the cap is properly associated with the body of the dialysis device. For example, a dialysis device can include haptic and aural feedback to indicate the cap is properly associated with the body of the dialysis device without any visual cues associated therewith.

Figure 5:
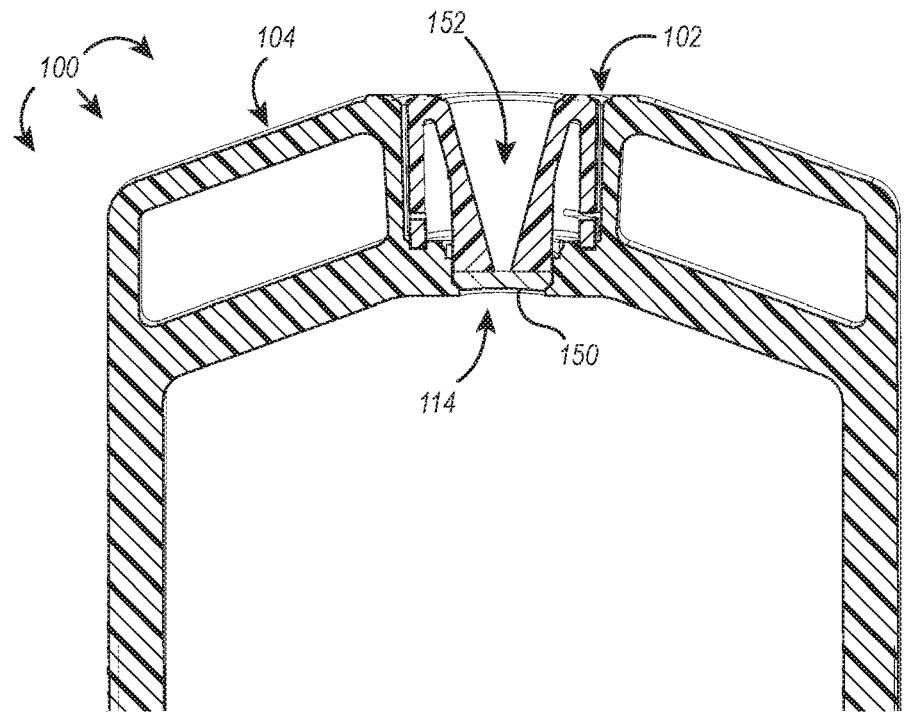
FIG. 5 illustrates a cross-section of a front elevation view of the dialysis device of FIG. 1.

Referring now to FIGS. 4 and 5, the cap 102 can include a bottom seal 150 coupled to the cap 102. In some embodiments, the bottom seal is over-molded with the cap. Alternatively, the bottom seal can be press fit to the cap or affixed to the cap using an adhesive (e.g., glue, paste, cement, epoxy resin, or similar). As shown in FIG. 5, the bottom seal 150 can abut and be compressed against the sidewalls defining the access port 114 to form a seal over the access port. The bottom seal can be made of any soft material, though in a preferred embodiment the bottom seal 150 is a self-sealing septum, as that term is defined below.

As used herein, the term "soft material," particularly when made with reference to the disclosed gaskets or seals, include those materials capable of elastic deformation in response to a force less than or equal to about 10 N and which can form a hermetic seal between at least two surfaces when in an elastically deformed state.

The term "hermetic seal," as used herein, includes any fluid-tight interaction between two or more surfaces and preferably includes any airtight interaction between two or more surfaces. For example, the sample chamber of the disclosed dialysis devices can be hermetically sealed between the frame (or gaskets associated therewith) and the dialysis membranes and/or between the access port and bottom seal when the cap is in a locked position, as these foregoing junctions are fluid-tight and preferably airtight.

Further, the term "self-sealing septum" includes any septum made of or including material that exhibits the ability to reseal and prevent leakage therethrough following mechanical disruption, particularly by puncturing (e.g., with an 18 G needle, 21 G needle, or smaller diameter—larger gauge—needle). Such self-sealing septa can include elastomeric closures made of or including materials obtained by vulcanization (cross-linking) polymerization, polyaddition, or polycondensation of macromolecular organic substances (e.g., elastomers). Ideally, self-sealing septa disclosed herein can be punctured (e.g., by a 21 G needle) by a force less than or equal to about 10 N, preferably less than or equal to about 5 N, up to at least two times, preferably up to at least 5 times, and more preferably up to at least 10 times, and maintain the ability to reseal and prevent leakage therethrough following each puncture.

In embodiments where the bottom seal 150 is a self-sealing septum or similar, such as that illustrated in FIG. 5, a needle and syringe can be used to remove sample from the sample chamber 112 (e.g., for testing or further processing). The dialysis device 100 includes a tapered needle channel 152 formed within the cap 102 as a safety precaution and for ease of removing sample from the device 100. Once the needle traverses the tapered needle channel 152, it can pierce the bottom seal to access the sample chamber 112, and upon removal of the needle from the bottom seal 150, a hermetic seal is reformed.

Figure 6:
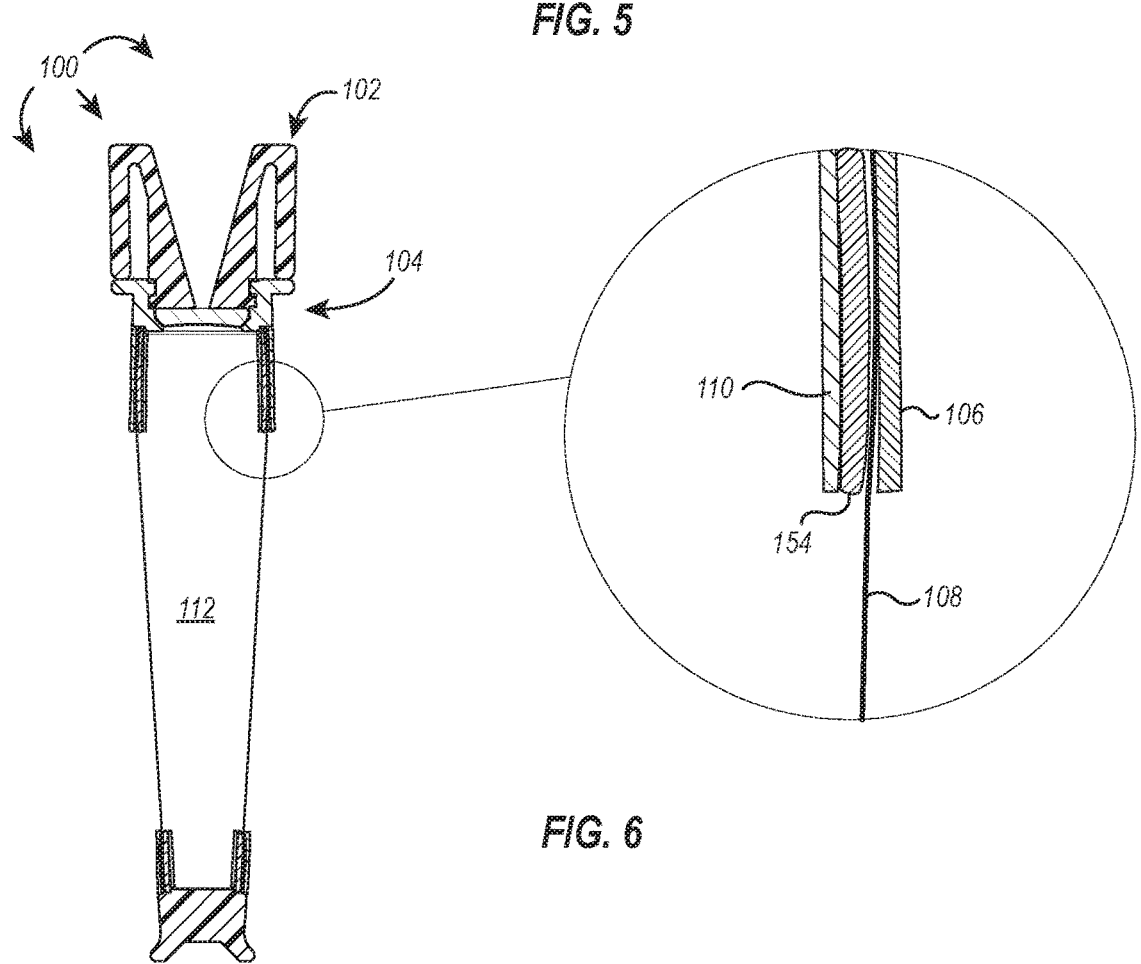
FIG. 6 illustrates a cross-section of a side elevation view of the dialysis device of FIG. 1.

FIG. 6 illustrates a cross-section of the dialysis device 100 with a magnified view of the component parts of the device 100 assembly, particularly the arrangement of components that form a hermetic seal between the dialysis membrane 108 and the frame 110. As shown in FIG. 6, the dialysis device 100 can include an internal frame 110 with an over-molded gasket 154 positioned between the frame 110 and the outer shell 106. The over-molded design maintains a slim profile of the frame 110 and gasket 154. In some embodiments, the gasket is coupled to the frame by an adhesive or other means known in the art.

The gasket 154 preferably includes or is made of a soft material and contributes to forming a hermetic seal between the dialysis membrane 108 and the frame 110 by elastically deforming in response to pressure exerted against it by the rigid outer shell 106 and rigid frame 110. The dialysis membrane 108 is sandwiched between the outer shell 106 and the deformed gasket 154 with sufficient force to retain the dialysis membrane 108 in connection with the gasket 154 when sample is loaded into the sample chamber 112 and to form and maintain a hermetic seal therebetween.

In some embodiments, the dialysis device includes additional gaskets or other components, such as gripping nubs, and can be assembled in any configuration disclosed and/or adapted from U.S. Pat. No. 9,248,407, which is incorporated herein by reference in its entirety (and duplicated in the Appendix attached hereto).

Additional Attachment Mechanisms

Dialysis devices of the present disclosure can include attachment mechanisms between the cap and device body that are different than that disclosed in FIGS. 1-6. For example, FIGS. 7, 8, 9, 10A, and 10B each illustrate different embodiments of dialysis devices that maintain at least some (or all) of the benefits described for the dialysis device 100 of FIGS. 1-6.

Figure 7:
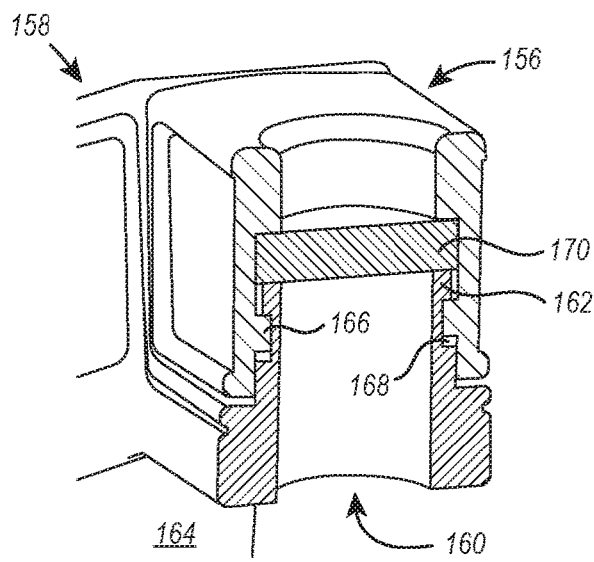
FIG. 7 illustrates a partial cross-section of a perspective view of another embodiment of a dialysis device incorporating features disclosed or envisioned herein.

FIG. 7 illustrates a partial cross-section of a cap 156 and dialysis device body 158 associated together to form a hermetic seal over an access port 160. As can be seen in FIG. 7, the body 158 includes an inner chamber or filler neck 162 that defines the access port 160 and is in fluid communication with the sample collection chamber 164. A pin 166 located on an interior sidewall of the cap 156 is configured to slide over the filler neck 162 and lock into a horizontal channel 168 formed on an exterior surface of the filler neck 162. In doing so, a self-sealing septum 170 associated with the cap 156 (e.g., over-molded, press-fit, or otherwise affixed) is biased against the mouth of the filler neck 162 with sufficient force to form a hermetic seal between the septum 170 and the filler neck 162.

In some embodiments, the pin 166 produces haptic and/or aural feedback when locking into the horizontal channel 168, thereby indicating that the cap 156 has properly formed a seal over the access port 160. As above, the haptic and/or aural feedback associated with securing the cap 156 decreases the likelihood of accidental spillage or leakage.

Figure 8:
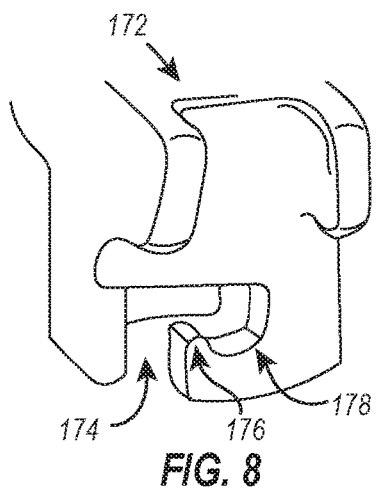
FIG. 8 illustrates a perspective view of another embodiment of a cap for use as part of a dialysis device incorporating features disclosed or envisioned herein.
Figure 9:
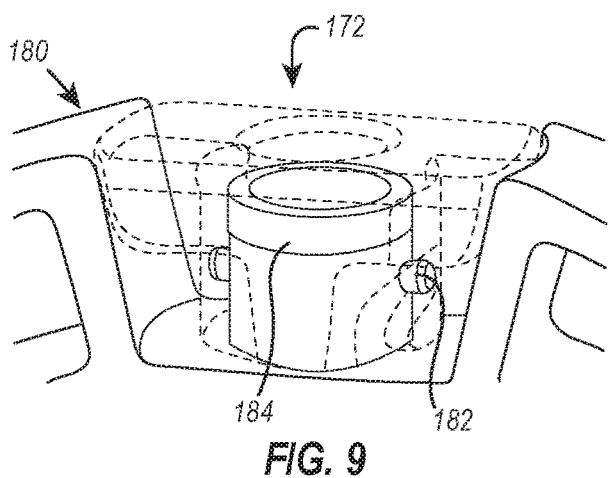
FIG. 9 illustrates a perspective view of the cap from FIG. 8, shown in a partially transparent view, associated with a dialysis device incorporating features disclosed or envisioned herein.

Instead of the pin being located on an interior sidewall of the cap and the filler neck having a channel disposed on an exterior surface to interact with the pin, as shown and described in FIG. 7, some embodiments of the present disclosure invert the orientation of the pin and channel such that the cap includes a channel that interacts with a pin extending from an exterior surface of the filler neck. FIGS. 8 and 9 are exemplary embodiments of the foregoing.

As shown in FIGS. 8 and 9, a cap 172 for use with dialysis devices disclosed herein can include a channel 174 defined by the sidewalls of the cap 172. The channel 174 can be configured to receive a pin 182 disposed on an exterior surface of a dialysis device body 180 (e.g., on the exterior surface of a filler neck). The channel 174 can further define a pressure ridge 176 that resists rotation of the cap about the pin, but in response to a locking force, the self-sealing septum 184 configured to flex and/or elastically deform and allow the pin 182 to pass into a locking portion 178 of the channel 174.

In some embodiments, the retention force of the pressure ridge 176 against the pin 182 within the locking portion 178 is sufficient to keep the cap 172 locked in position. The cap 172 can be locked, for example, in a sealed position where the cap 172 seals an access port (not shown) using a soft material, preferably a self-sealing septum 184.

The cap 172 can be unsealed and removed by twisting the cap 172 and applying an unlocking force against the pressure ridge 176, which causes the self-sealing septum 184 to flex and/or elastically deform and thereby release the pin 182 from the locking portion 178 of the channel 174. In some embodiments, the interaction between the pin 182 and the pressure ridge 176 (e.g., passing over the ridge 176 and into the locking portion 178) can produce haptic and/or aural feedback, thereby indicating that the cap 172 has properly formed a seal over the access port. As above, the haptic and/or aural feedback associated with securing the cap 172 can decrease the likelihood of accidental spillage or leakage.

Figure 10A:
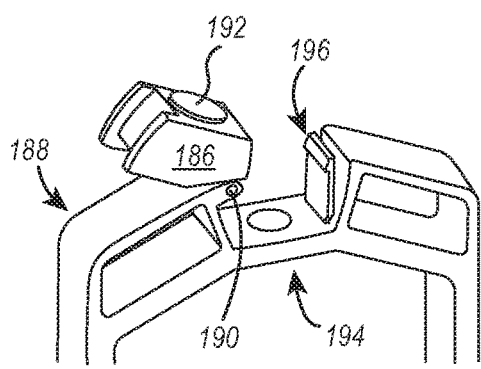
FIG. 10A illustrates a perspective view of an open configuration of still yet another embodiment of a dialysis device incorporating features disclosed or envisioned herein.
Figure 10B:
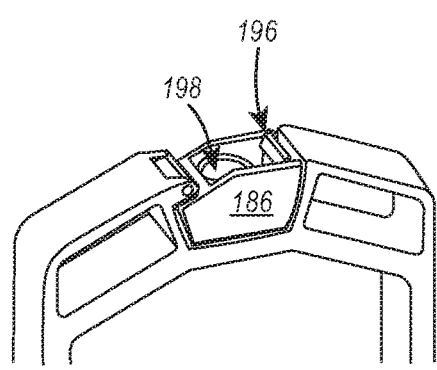
FIG. 10B illustrates a perspective view of a closed configuration of the dialysis device of FIG. 10A.

Referring now to FIGS. 10A and 10B, illustrated is an embodiment of the present disclosure that includes a cap 186 attached to the body 188 of a dialysis device by a hinge joint 190. The cap 186 includes a gasket 192 made of soft material that is sized and shaped to form a seal over the access port 194 when the cap 186 is rotated (via the hinge joint 190) and secured over the access port 194. In some embodiments, the gasket 192 is a self-sealing septum, and the cap 186 can include a needle channel 198 for receiving and guiding a needle to the self-sealing septum where the needle can be used to pierce the self-sealing septum and extract sample from the sample chamber.

In some embodiments, securing the cap 186 over the access port 194 includes locking the cap 186 with a flexible lock 196, which is depicted in FIGS. 10A and 10B as a flexible piece of plastic having a flange positioned thereon to secure a top surface of the cap 186 and prevent rotation of the cap 186 away from the access port 194. The cap 186 can be unsecured from the access port 194, for example, by pushing the flexible lock 196 away from the cap 186 such that the lock 196 no longer engages the top surface of the cap 186 and/or by rotating the cap 186 away from the access port 194 after the lock 196 has been disengaged.

It should be appreciated that securing and releasing the flexible lock 196 can produce haptic and/or aural feedback, thereby indicating that the cap 186 has properly formed a seal over the access port 194. As above, the haptic and/or aural feedback associated with securing the cap 186 can decrease the likelihood of accidental spillage or leakage.

Exemplary Sensor Caps

The dialysis devices disclosed herein provide significant benefits and improvements over prior dialysis devices, many of which were discussed above. However, there are additional problems left unsolved by the foregoing dialysis devices. For example, it is difficult to measure properties of the sample within the sample chamber without (1) removing an aliquot of sample from the sample chamber to interrogate externally or (2) removing the lid and introducing an external meter directly into the sample. In either case, the dialysis device is removed from the dialysate for the period of time required to withdraw the aliquot or to retrieve a measurement from the meter. This is an inefficient use of time and resources. Because the sample was removed from the dialysate for a period of time, any diffusion, ion exchange, or other benefit that could have been realized by dialyzing the sample during that period of time did not take place. This often means the sample is dialyzed for an additional period of time equivalent (or greater) to the time the sample was removed from the dialysate. This effectively make the dialysis time longer than it otherwise would have been and breeds inefficiencies into the dialysis protocol, which can be compounded if multiple (e.g., serial) aliquots or sample measurements are taken.

There are additional inefficiencies and problems with the current methods for measuring a property of the sample within the dialysis device. For example, in the case where an aliquot of sample is removed from the sample chamber for interrogation, each aliquot that is removed is necessarily sacrificed and lost. This negatively impacts sample yield. Furthermore, the sample can be contaminated during extraction of an aliquot. If the aliquot is removed using a pipetting device, the sample chamber is unsealed to allow for sample extraction and consequently exposed to environmental contaminants or contaminants introduced during pipetting. If the aliquot is removed using a needle and syringe, a non-sterile needle could introduce contaminants into the sample chamber. In either case, sample is lost in the process and is subjected to potential contamination.

In the case where an external meter is used to measure a property of the sample directly within the sample chamber, as above, the sample is again subjected to a contamination risk—both from the environment and from the meter, itself. Remnants of previous reads can be introduced by the meter into the sample, and could negatively impact the dialysis protocol, sample purity, or even sample integrity.

The sample is also at risk of suffering loss or contamination due to user errors. In accordance with known methods and systems, the use of an external meter to directly test a property of the sample within the sample chamber requires removal of the cap and/or breaking the hermetic seal of the sample chamber (e.g., introducing the meter through the unsealed access port to measure sample properties directly). Without the dialysis device being sealed, mistakes made by the user or others within the user's environment can cause a loss or contamination of the sample. For example, if the user inadvertently knocked over the dialysis device while the device is unsealed, large volumes of sample could be lost or contaminated. Similarly, if the device is left open, the sample has a greater chance of receiving an airborne contaminate.

Accordingly, there are problems in the art of sample monitoring during dialysis that can be addressed.

Embodiments of the present disclosure solve one or more of the foregoing problems in the art of sample monitoring, particularly within dialysis devices. In one embodiment, shown in FIG. 11, a dialysis device 200 includes a sensor cap 202 having a probe 204 integrally formed or otherwise coupled to the sensor cap 202 such that when the sensor cap 202 is tightly associated with the body 206 of the dialysis device 200 (e.g., hermetically sealing the sample chamber 208), the associated probe 204 extends into the sample chamber 208. Using the attached probe 204, the sensor cap 202 can monitor one or more properties of the fluid within the sample chamber 208 in real-time and in a controlled manner and wirelessly transmit the properties or data derived therefrom to a destination computing device. In this way, the disclosed sensor caps enable real-time monitoring of sample solution parameters, which can, among other things, more accurately indicate when dialysis is complete—saving time and minimizing sample waste.

Embodiments of the sensor cap provided herein provide additional benefits. For example, the disclosed sensor caps reduce the likelihood of contaminating the sample. The sensor cap significantly reduces or eliminates the prior need to open the dialysis device during dialysis (e.g., to remove an aliquot of sample/fluid or to introduce a meter to interrogate properties of the sample/fluid within the sample chamber). Because the dialysis device remains hermetically sealed instead of being routinely probed or opened, there are fewer opportunities for contaminants to be introduced into the sample chamber. Accordingly, the dialyzed samples are more likely to be contaminant free than samples dialyzed using other known dialysis devices and systems.

Furthermore, as alluded to above, the sensor caps disclosed herein can also significantly reduce or eliminate sample waste. There is no longer a need to remove an aliquot of sample so that properties of the sample chamber fluid can be measured and/or tracked throughout the dialysis protocol. Instead, the sensor cap receives data directly from the probe, which can be concurrently measuring properties of the fluid in the sample chamber and transmitting those data to a destination computing system where they can be reviewed.

Figure 12:
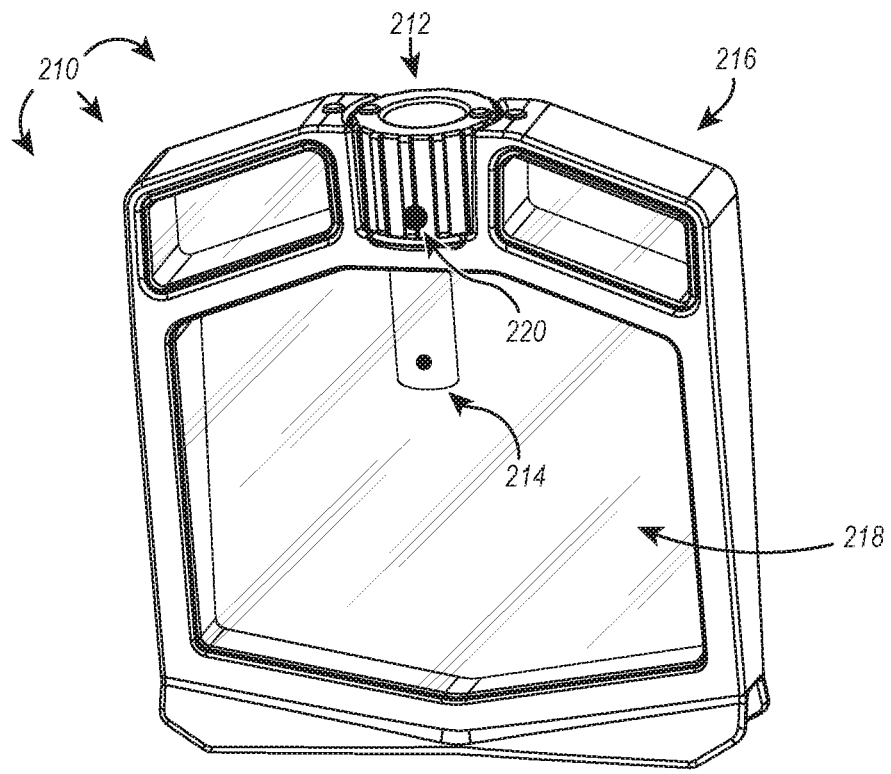
FIG. 12 illustrates a perspective view of another embodiment of a sensor cap in association with a dialysis device and incorporating features disclosed or envisioned herein.

In some embodiments, it could also be advantageous to monitor properties of a fluid outside of the sample chamber, such as the dialysate. As shown in FIG. 12, a dialysis device 210 includes a sensor cap 212 having a probe 214 integrally formed or otherwise coupled to the sensor cap 212, in the same or similar manner as the sensor cap 202 and associated probe 204 discussed above. The dialysis device 210 can additionally incorporate a second probe 220 into the cap body that is configured to measure properties of a fluid disposed outside the sample chamber 218, such as the dialysate. Using the attached probe 214, the sensor cap 212 can monitor one or more properties of the fluid within the sample chamber 218 in real-time and in a controlled manner and wirelessly transmit the properties or data derived therefrom to a destination computing device. Similarly, using the attached probe 220, the sensor cap 212 can (simultaneously or serially) monitor one or more properties of a fluid disposed outside the sample chamber 218 in real-time and in a controlled manner and wirelessly transmit the properties or data derived therefrom to the same or different destination computing device. In this way, the disclosed sensor caps enable real-time monitoring of sample solution and dialysate parameters, which can, among other things, indicate optimal times to change dialysate or other buffers to more efficiently dialyze sample in less time.

In some embodiments, the second probe 220 is positioned on a lower portion of the sensor cap where the second probe 220 is more likely to interact with dialysate. In some embodiments, the buoyancy of the dialysis device 210 is adjusted so that a greater proportion of the device 210 is submerged in the dialysate. This can also act to increase the likelihood that the second probe 220 interacts with dialysate. Buoyancy can be adjusted by, for example, adding weights to the device or reducing the volume of gas, foam, or similar in the float chambers.

Figure 11:
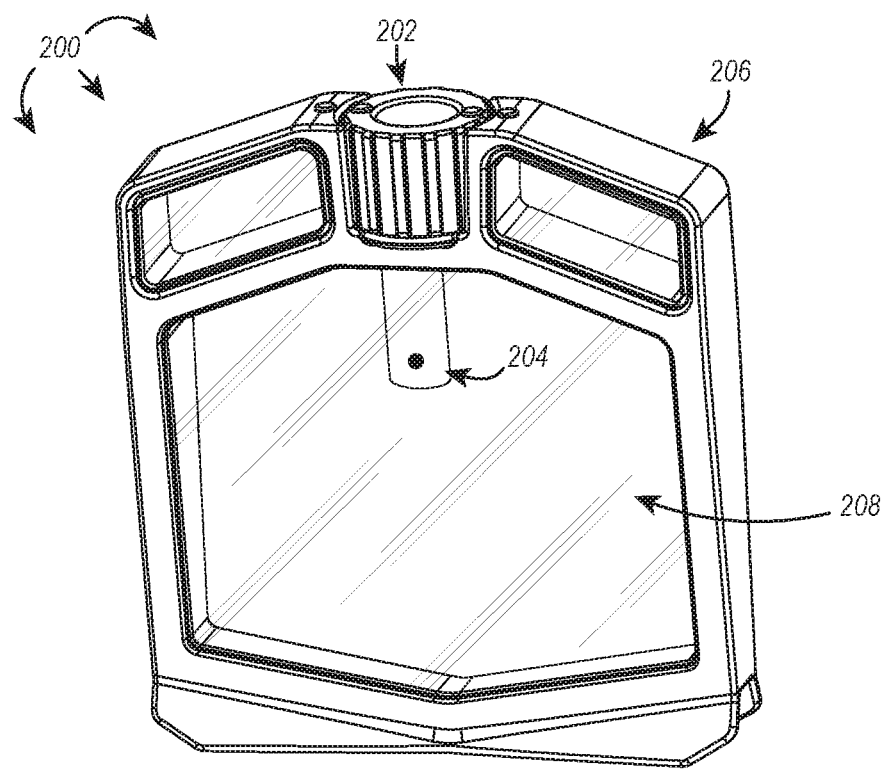
FIG. 11 illustrates a perspective view of one embodiment of a sensor cap in association with a dialysis device and incorporating features disclosed or envisioned herein.

It should be appreciated that the dialysis devices 200, 210 of FIGS. 11 and 12 can include any combination of elements described above, including those elements shown and described in FIGS. 1-10B and can additionally benefit from any of the advantages inherent or described, particularly those shown and described in FIGS. 1-10B. As a non-specific example, the dialysis devices 200, 210 can incorporate any combination of visual cues, aural feedback, and haptic feedback described above and can include any type of cap-body attachment mechanism described or envisioned herein.

Further, in some embodiments, the components of the internal and/or external probes may larger than the space provided within the sensor cap, such as those shown in FIGS. 11 and 12. Accordingly, alternatively dimensioned sensor caps are envisioned within the scope of this disclosure. For example, a bulbous sensor cap extending above the top of the dialysis device could be used to house larger and/or additional components such as printed circuit boards, transceivers (or separate transmitters and receivers), sensor circuitry, power sources, and/or switches. Depending on the additional weight and/or distribution of weight resulting from the alternatively dimensioned sensor cap, the dialysis device may include additional float chambers and/or increase the volume of the float chambers present to offset the added/altered weight of the combined dialysis device and sensor cap. In some embodiments, the sensor cap is augmented to include one or more float chambers positioned within or otherwise associated with the sensor cap to offset any additional weight or imbalance caused by the larger and/or heavier sensor cap. Preferably, the rebalancing of the float chambers within the dialysis device and/or sensor cap is performed to allow the dialysis device to remain upright during dialysis, thereby maximizing the surface area of the membrane exposed to dialysate.

Figure 13:
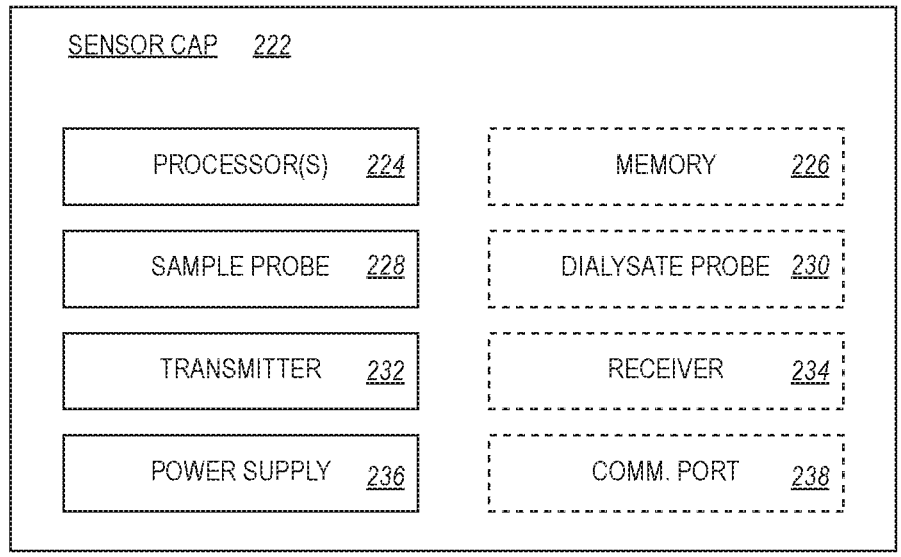
FIG. 13 illustrates a schematic of components associated with one embodiment of a sensor cap incorporating features disclosed or envisioned herein.

Referring now to FIG. 13, illustrated is a schematic of components associated with one embodiment of a sensor cap 222 incorporating features disclosed or envisioned herein. As shown, the sensor cap 222 can include one or more processors 224 in electrical communication with a sample probe 228 and a transmitter 232. The sensor probe can measure one or more properties of the fluid from the sample chamber, which can include, for example, any of pH, conductivity, dissolved oxygen concentration, electrical resistance, temperature, protein concentration, UV absorbance, redox potential, or turbidity. The measurements obtained by the sample probe 228 can, in one embodiment, be passed directly to the transmitter 232 where the raw measurement data are sent to a destination computing system. Alternatively, the raw measurement data can be pre-processed by the one or more processors and then sent to a destination computing system.

In some embodiments, the sensor cap 222 includes a local memory storage device 226 that can be used to store (pre- or post-processed) measurement data and/or computer-executable instructions that enable the sensor cap 222 to perform a variety of functions such as what properties to measure and at what times, transmission instructions or credentials for the destination device and/or different methodologies for processing received data, etc.

In some embodiments, and as described above with respect to FIG. 12, a sensor cap 222 can additionally include a dialysate probe 230. The dialysate probe 230 can be in electrical communication with the same (or different) processor(s) as the sample probe 228 and can have a dedicated or shared transmitter 232. In some embodiments, the transmitter 232 is a transceiver.

Alternatively, the sensor cap 222 can include a standalone receiver 234 configured to receive instructions from a control computing device or from a destination computing device, such as a user's smart phone. The received instructions can be processed by the one or more processors 224 to execute any of function or method described herein or known in the art. In some embodiments, the sensor cap includes a receiver, a processor, and a local memory storage device and can wirelessly receive instructions from a control computing device to, for example, take measurements using the sample probe 228 and to store the measurements on the local memory storage device for later retrieval. Alternatively, the measurements can be transmitted back to the control computing device using a transmitter 232.

In embodiments where the gathered data are stored locally, the associated sensor cap can additionally include a communication port 238 (e.g., a micro-USB port or other port known in the art) for rapid wire-based transfer of data from the sensor cap to a destination computing system. For example, a dialysis device having a sensor cap that collects and locally stores data about the dialysate and/or sample fluid can be temporarily anchored to a side of the beaker where it is dialyzing and manually wired to a destination computing device via the communication port associated with the sensor cap. Once the data are retrieved from the sensor cap, the dialysis device can be unanchored from the side of the beaker and return to unhindered dialysis.

Additionally, or alternatively, the communication port 238 can be used to connect to a wireless transmitter, which transmits the gathered and/or locally stored data from the sensor cap to a destination computing system.

It should be appreciated that in some embodiments the activities of the sensor cap can be pre-programmed and stored locally. In other embodiments, the activities of the sensor cap are provided by a control computing device and can be adapted based on a potentially evolving status of the measured fluid.

As shown in FIG. 13, the sensor cap 222 can additionally include a power supply 236 for providing electrical power to any and/or all of the components of the sensor cap 222. In one embodiment, the power supply 236 includes rechargeable batteries. Alternatively, the power supply 236 can include disposable batteries. Particularly in the latter embodiment, the sensor cap can have an access panel that provides access to the power supply (e.g., disposable batteries) without exposing other electronic components of the sensor cap. In some embodiments, one or more additional components of the sensor cap are disposable. For example, the probe may be disposable or interchangeable to prevent contamination during reuse. In some embodiments, the whole sensor cap is disposable or intended for a single use.

Systems for Performing and Monitoring Dialysis of a Sample

Figure 14:
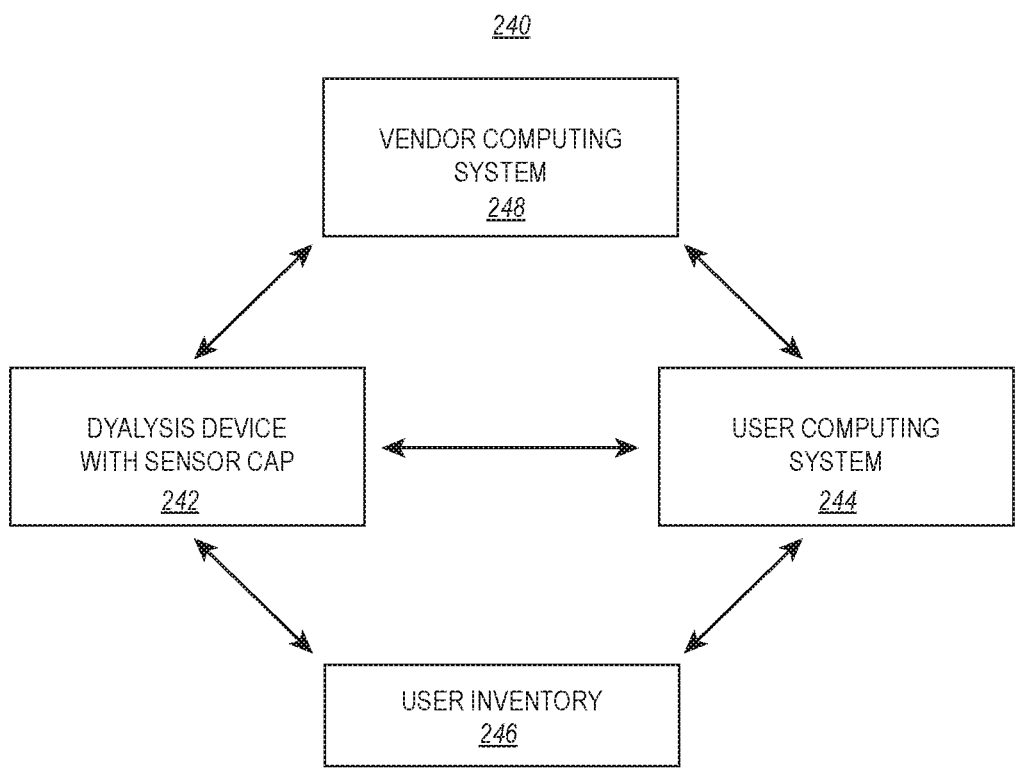
FIG. 14 illustrates a schematic of a system that includes a sensor cap incorporating features disclosed or envisioned herein.

In accordance with the foregoing, sensor caps of the present disclosure can be incorporated into dialysis devices and used to monitor dialysis conditions in real time. In some embodiments, such dialysis devices can be part of a system for performing and monitoring the dialysis of a sample. For example, as shown in FIG. 14, a system 240 for performing and monitoring the dialysis of a sample can include a dialysis device with a sensor cap 242 in communication with a user computing system 244 (e.g., a destination computing device). The user computing system 244 can include, for example, a mobile device running a mobile application or a remote computer system operating a local or cloud-based software program that allows the user to track real-time or near real-time progress of sample/dialysate properties measured by the dialysis device and sensor cap 242 to determine when the sample reaches equilibrium with the dialysate, indicating that either dialysis is complete (e.g., reached a final desired concentration) or the dialysate should be changed to complete the buffer exchange (e.g., achieve a desired endpoint).

In some embodiments, the user can set a trigger condition (e.g., a given pH, temperature, a rate of change of conductivity, or conductivity threshold), and when the sensor cap or user computing system identifies the trigger condition as being met, an alert can be sent to the user (e.g., a text message, e-mail, or telephone call) identifying the trigger condition has been met or exceeded. Alternatively, after the dialysis device and sensor cap 242 and/or user computing system 244 identifies the trigger condition as being met, the dialysis device and sensor cap 242 and/or user computing system 244 can change one or more dialysis conditions such as a stirring speed, a dialysis time, a time of a particular dialysis step, or a temperature, volume, chemistry, or concentration of one or more parts of the dialysate.

The system 240 can additionally enable communication between the dialysis device and sensor cap 242 and/or the user computing system 244 with a user inventory database 246 to track the usage and availability of consumable products (e.g., dialysis buffers, dialysis devices, dialysis membranes or dialysis devices having particular types or porosity sizes of dialysis membranes, sensor caps, probes) within the user's organization or laboratory. The user computing system 244 or user inventory database 246 may be associated with one or more rules that prompt the user to purchase additional consumable goods (or simply cause a purchase to be made) when a threshold or trigger condition is met.

As an exemplary working example, the user computing system 244 can receive data from the dialysis device and sensor cap 242 identifying the dialysis device being used and the dialysate being used in a current dialysis protocol. Upon querying the user inventory database 246, it is determined that there is only one remaining dialysis device in inventory and that the volume of dialysate in inventory is sufficient to complete two more dialysis protocols similar to the one being performed. Having only a single dialysis device remaining in inventory causes a trigger condition to be met, and in response, the user computing system 244 automatically contacts a vendor computing system 248 and requests or acquires the requisite information to automatically fill out a purchase order for additional dialysis devices. The completed purchase order is then sent to the user for approval. The volume of dialysis buffer remaining in inventory causes a different trigger condition to be met, and in this instance, an order for additional dialysis buffer is automatically processed by the user computing system 244 at the vendor computing system 248. In this way, the system can streamline workflow and inventory management more efficiently and with as much user interaction or automation throughout the process as desired (e.g., from no user interaction to complete user oversight of all decision making).

It should also be appreciated that any number or type of trigger conditions associated with systems described herein can be pre-determined and/or changed to meet individual user requirements or preferences.

The sensor caps and/or destination computing systems of the present invention may comprise, utilize, or communicate with a special purpose or general-purpose computer including computer hardware. The sensor caps or related computer systems within the scope of the present invention can also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media (e.g., hardware storage devices). Computer-readable media that carry computer-executable instructions are transmission media. Thus, by way of example, and not limitation, embodiments of the invention can comprise at least two distinctly different kinds of computer-readable media: computer-readable hardware storage media and transmission computer-readable media.

Computer-readable hardware storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

The sensor cap can be a "smart device" such that it is capable of communicating and sharing information between multiple devices over a network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry desired program code in the form of computer-executable instructions or data structures and which can be accessed by a general purpose or special purpose computer. Combinations of the above are also included within the scope of computer-readable media.

Further, upon reaching various computer system components, program code in the form of computer-executable instructions or data structures can be transferred automatically from transmission computer-readable media to computer-readable hardware storage media (or vice versa). For example, computer-executable instructions or data structures received over a network or data link can be buffered in RAM within a network interface module (e.g., a "NIC"), and then eventually transferred to computer system RAM and/or to less volatile computer-readable hardware storage media at a computer system. Thus, computer-readable hardware storage media can be included in computer system components that also (or even primarily) utilize transmission media.

Computer-executable instructions comprise, for example, instructions and data which cause a general purpose computer (e.g., destination computing devices), special purpose computer (e.g., sensor caps and/or destination computing devices), or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, sensor caps, personal computers, desktop computers, laptop computers, message processors, hand-held devices, multiprocessor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, wireless communication between any of the disclosed computer systems (e.g., between sensor caps and destination computing devices) can be performed using any wireless protocol known in the art, including, for example, Bluetooth, ZigBee, ultra-wideband (UWB), and Wi-Fi. Accordingly, it should be appreciated that if a particular wireless protocol (or associated components) is particularly noted or described within any of the disclosed embodiments, the particular wireless protocol noted can be interchanged with any other wireless protocol known in the art while maintaining any disclosed functionality and/or performing the same or a substantially similar task associated therewith.

Methods for Monitoring Dialysis of a Sample

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed. Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Figure 15:
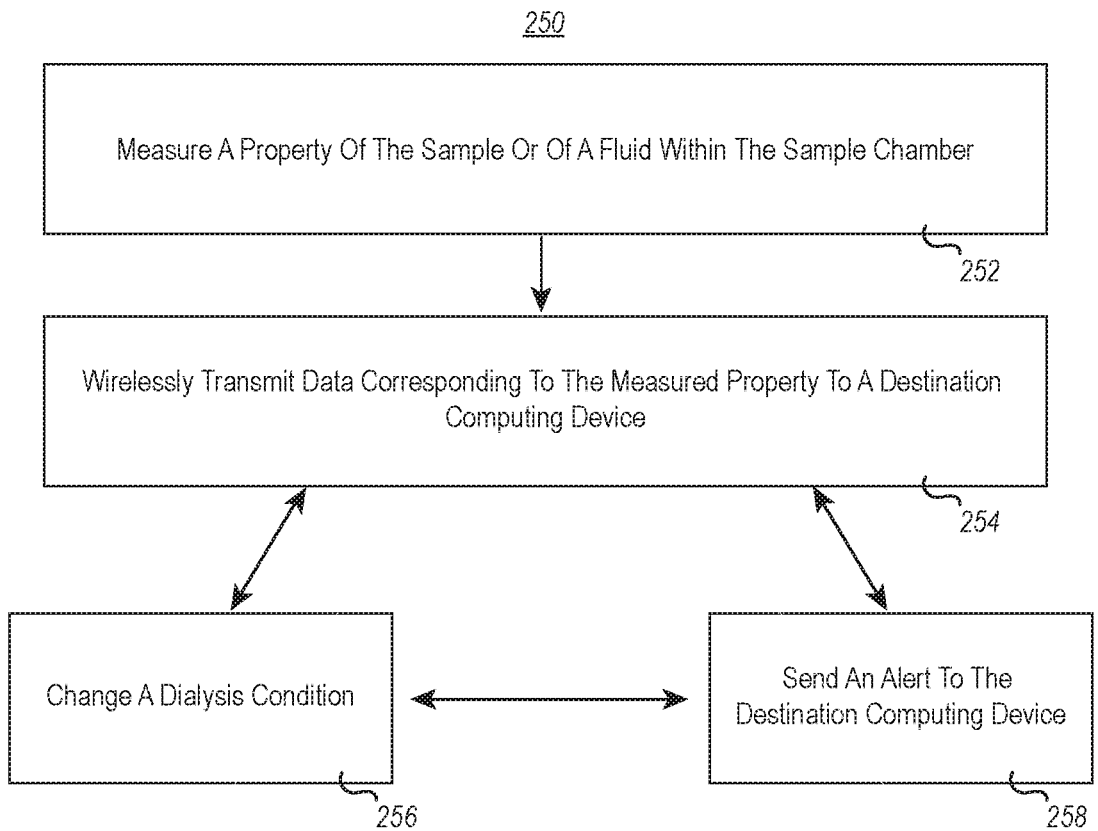
FIG. 15 illustrates a flowchart of a method performed by one or more components of the system of FIG. 14.

Referring now to FIG. 15, a method 250 is illustrated that includes acts for monitoring the dialysis of a sample.

The method 250 includes measuring a property of the sample or of a fluid within the sample chamber (act 252). Act 252 can be implemented, for example, using any of the dialysis devices having sensor caps associated therewith. The act of measuring a property of the sample can be performed by the probe portion of the sensor cap, which extends into the sample chamber of the dialysis device. Examples of this are discussed above with respect to FIGS. 11-12, and example properties to be measured include, among other things, pH, conductivity, dissolved oxygen concentration, electrical resistance, temperature, protein concentration, UV absorbance, redox potential, or turbidity.

The method 250 also includes wirelessly transmitting data corresponding to the measured property to a destination computing device (act 254). Act 254 can be implemented, for example, by a sensor cap as described and illustrated in FIGS. 11-13. Particularly, act 254 can be implemented by a transmitter or transceiver associated with the sensor cap and can be carried out using any wireless protocol, as discussed above.

The method 250 also includes changing a dialysis condition (256). Act 256 can be implemented, for example, by a destination computing device in response to act 256. The destination computing device can include a user computing device (e.g., a smart phone or user PC) in electrical communication with a control unit that can affect one or more of a stirring speed, a dialysis time, or a temperature, volume, chemistry, or concentration of one or more parts of the dialysate.

The method 250 also includes sending an alert to the destination computing device (act 258). Act 258 can be implemented, for example, by the dialysis device or user computing device, as discussed above with respect to FIG. 14. The destination computing device can be, for example, a user's mobile device or a server hosting the user's email account. The alert can be any alert described above, including, as non-limiting examples, an indication that the dialysis is complete or needs buffer changed, an authorization to purchase consumables, or a notification and/or receipt for goods purchased.

It is to be understood that features described with regard to the various embodiments herein may be mixed and matched in any desired combination. In addition, the concepts disclosed or envisioned herein may be embodied in other specific forms. The described embodiments are to be considered in all respects only as illustrative and not restrictive. The scope is, therefore, indicated by the appended claims rather than by the foregoing description. All changes which come within the meaning and range of equivalency of the claims are to be embraced within their scope.

EXAMPLE

An exemplary dialysis device of the present disclosure having a sensor cap associated therewith (e.g., as shown in FIG. 11) was used to dialyze a solution of phosphate-buffered saline (PBS) to demonstrate various aspects of the functionality and utility of the dialysis device and sensor cap. Twenty-five milliliters of Dulbecco's PBS (DPBS) was placed in the sample chamber of the dialysis device, and the sensor cap was secured to the dialysis device. The probe of the sensor cap was at least partially submerged in (i.e., in contact with) the solution within the sample chamber, and an initial measurement was observed to confirm conductivity.

The DPBS-loaded dialysis device was placed in a 5 L water bath and dialyzed in three stages: (1) a 2.5 hour dialysis period after which the water was exchanged and (2) dialysis was continued overnight (e.g., 17 hours); the water was again exchanged after the overnight dialysis period and (3) dialysis was continued for an additional 3 hours.

Figure 16:
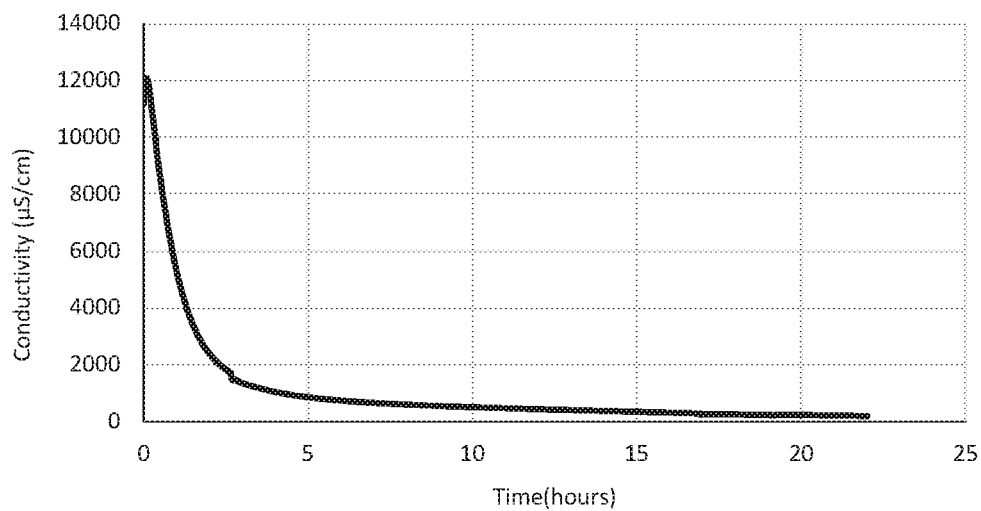
FIG. 16 illustrates a chart of the measured conductivity of a solution within an exemplary dialysis device over time using an exemplary sensor cap of the present disclosure.

Conductivity measurements of the solution within the sample chamber were continuously measured and transmitted by the sensor cap throughout the three-stage dialysis periods. A graph illustrating these data is provided in FIG. 16. As shown, greater than 97% of the DPBS was exchanged after about 22 hours of dialysis, demonstrating both the efficient dialysis performable by a dialysis device of the present disclosure and the accurate hands-free conductivity monitoring capability of the associated sensor cap. A measure of fluid from the sample chamber was taken at the end of dialysis and measured using an aquatwin conductivity meter for comparison. The conductivity measurements between the sensor cap and the separate conductivity meter were substantially similar, validating the accuracy of the sensor cap.

What is claimed is:

1. A system comprising:
a dialysis device, comprising:
a frame comprising a plurality of sidewalls impermeable to a sample being dialyzed;
a pair of dialysis membranes, wherein each dialysis membrane of the pair of dialysis membranes is associated with an opposing face of the plurality of sidewalls such that the plurality of sidewalls and the pair of dialysis membranes define a sample chamber, and wherein a first sidewall of the plurality of sidewalls defines an access port in fluid communication with the sample chamber; and
an outer shell surrounding at least a portion of the pair of dialysis membranes; and
a sensor cap, comprising:
a body having a closed end;
an attachment mechanism coupled to the body and configured to provide aural and haptic feedback when the sensor cap forms a tight association with the dialysis device by securing over the access port of the dialysis device to seal the sample chamber of the dialysis device formed by the plurality of sidewalls of a frame of the dialysis device and the pair of dialysis membranes, wherein the attachment mechanism comprises a channel defined by a sidewall of the sensor cap, the channel configured in size and shape to receive a pin disposed on an exterior surface of the dialysis device, and wherein the sidewall of the sensor cap further defines a pressure ridge configured (i) to resist rotation of the sensor cap about the pin, (ii) to allow the pin to pass into a locking portion of the channel in response to a locking force that causes flexing or deformation of the pressure ridge, and (iii) to release the pin from the locking portion of the channel in response to an unlocking force that causes flexing or deformation of the pressure ridge;
one or more processors;
a probe in electrical communication with the one or more processors, the probe being configured to measure a property of a fluid;
a transmitter; and
a power supply in electrical communication with the one or more processors, the probe, and the transmitter,
wherein the body of the sensor cap forms a fluid-tight seal around a cavity comprising the one or more processors, the transmitter, and the power supply.

2. The system of claim 1, wherein the first sidewall of the plurality of sidewalls comprises a concave curvature with respect to the sample chamber partially defined thereby and defines the access port in fluid communication with the sample chamber.

* * * * *